United States Patent
Hahn et al.

(10) Patent No.: US 9,624,286 B2
(45) Date of Patent: Apr. 18, 2017

(54) COMPOSITION COMPRISING PEPTIDE DERIVED FROM ADIPONECTIN

(71) Applicants: KNU-INDUSTRY COOPERATION FOUNDATION, Chuncheon-si, Gangwon-do (KR); SUPADELIXIR INC., Chuncheon-si, Gangwon-do (KR)

(72) Inventors: Jang-Hee Hahn, Chuncheon-si (KR); Dong-Young Lim, Chuncheon-si (KR)

(73) Assignees: KNU-INDUSTRY COOPERATION FOUNDATION, Chuncheon-si, Gangwon (KR); SUPADELIXIR INC., Chuncheon-si, Gangwon (KR)

( * ) Notice: Subject to any disclaimer, the term of this patent is extended or adjusted under 35 U.S.C. 154(b) by 0 days.

(21) Appl. No.: 15/022,093

(22) PCT Filed: Sep. 12, 2014

(86) PCT No.: PCT/KR2014/008497
§ 371 (c)(1),
(2) Date: Mar. 15, 2016

(87) PCT Pub. No.: WO2015/041430
PCT Pub. Date: Mar. 26, 2015

(65) Prior Publication Data
US 2016/0222077 A1 Aug. 4, 2016

(30) Foreign Application Priority Data
Sep. 17, 2013 (KR) .................. 10-2013-0111502

(51) Int. Cl.
| | | |
|---|---|---|
| *A61K 38/00* | (2006.01) | |
| *A61K 8/64* | (2006.01) | |
| *A61K 38/06* | (2006.01) | |
| *A61K 38/07* | (2006.01) | |
| *A61K 38/08* | (2006.01) | |
| *A61Q 19/02* | (2006.01) | |
| *A61Q 19/08* | (2006.01) | |
| *C07K 7/06* | (2006.01) | |
| *C07K 5/08* | (2006.01) | |
| *C07K 5/10* | (2006.01) | |
| *C07K 14/575* | (2006.01) | |
| *C07K 5/087* | (2006.01) | |
| *C07K 5/097* | (2006.01) | |
| *C07K 5/103* | (2006.01) | |
| *C07K 5/107* | (2006.01) | |
| *A61Q 19/00* | (2006.01) | |

(52) U.S. Cl.
CPC .............. *C07K 14/575* (2013.01); *A61K 8/64* (2013.01); *A61Q 19/007* (2013.01); *A61Q 19/08* (2013.01); *C07K 5/0812* (2013.01); *C07K 5/0821* (2013.01); *C07K 5/101* (2013.01); *C07K 5/1016* (2013.01); *C07K 14/5759* (2013.01); *A61K 38/00* (2013.01)

(58) Field of Classification Search
CPC .......... A61K 38/00; A61K 8/64; A61K 38/06; A61K 38/07; A61K 38/08; A61Q 19/02; A61Q 19/08; A61Q 19/007; C07K 14/575; C07K 7/06; C07K 5/08; C07K 5/0812; C07K 5/0821; C07K 5/10; C07K 5/101; C07K 5/1016
USPC .... 514/18.7, 17.4, 21.9, 21.8; 530/328, 330, 530/331; 424/62; 435/29
See application file for complete search history.

(56) References Cited

U.S. PATENT DOCUMENTS

| | | | | |
|---|---|---|---|---|
| 5,599,907 A | * | 2/1997 | Anderson | ........ A61K 47/48307 435/69.1 |
| 7,026,443 B1 | * | 4/2006 | Sette | ...................... A61K 39/12 424/184.1 |
| 7,807,180 B2 | * | 10/2010 | Lu | ........................ A61K 39/285 424/184.1 |
| 7,863,243 B2 | | 1/2011 | Matsuzawa et al. | |
| 8,314,061 B2 | | 11/2012 | Morrow et al. | |
| 8,637,035 B2 | * | 1/2014 | Wu | ..................... C07K 16/1081 424/159.1 |
| 8,821,871 B2 | * | 9/2014 | Van Ryn | ................ C07K 16/44 424/133.1 |
| 2006/0247169 A1 | | 11/2006 | Matsuzawa et al. | |
| 2009/0175923 A1 | * | 7/2009 | Shafer | ..................... C07K 16/18 424/423 |
| 2009/0197806 A1 | | 8/2009 | Morrow et al. | |

FOREIGN PATENT DOCUMENTS

| | | |
|---|---|---|
| JP | 2004-331590 A | 11/2004 |
| JP | 2004-345968 A | 12/2004 |
| JP | 2009-523173 A | 6/2009 |
| KR | 10-2010-0100708 A | 9/2010 |
| WO | 2005/042007 A1 | 5/2005 |

OTHER PUBLICATIONS

A0A0E9U2B9 from UniProt, pp. 1-3. Integrated into UniProtKB Jun. 24, 2015.*

(Continued)

*Primary Examiner* — Julie Ha
(74) *Attorney, Agent, or Firm* — Vorys, Sater, Seymour & Pease LLP; Mih Suhn Koh

(57) ABSTRACT

Provided is a pharmaceutical or cosmetic composition comprising adiponectin-derived peptide fragments, i.e., the peptides of SEQ ID NOs: 1 to 6 as an active ingredient. The peptides facilitate skin regeneration and moisturization, inhibit skin wrinkle, and have inhibitory activities against allergy and inflammation as well as metastasis of cancer cells.

4 Claims, 9 Drawing Sheets

(56) References Cited

OTHER PUBLICATIONS

Q7M2G0 from UniProt, pp. 1-3. Integrated into UniProtKB Dec. 15, 2003.*
A0A0E9S468 from UniProt, pp. 1-3. Integrated into UniProtKB Jun. 24, 2015.*
A0A0E9SEB0 from UniProt, pp. 1-3. Integrated into UniProtKB Jun. 24, 2015.*
T0JZD0 from UniProt, pp. 1-4. Integrated into UniProtKB Oct. 16, 2013.*
A0A0W0FEH7 from UniProt, pp. 1-3. Integrated into UniProtKB Mar. 16, 2016.*

* cited by examiner

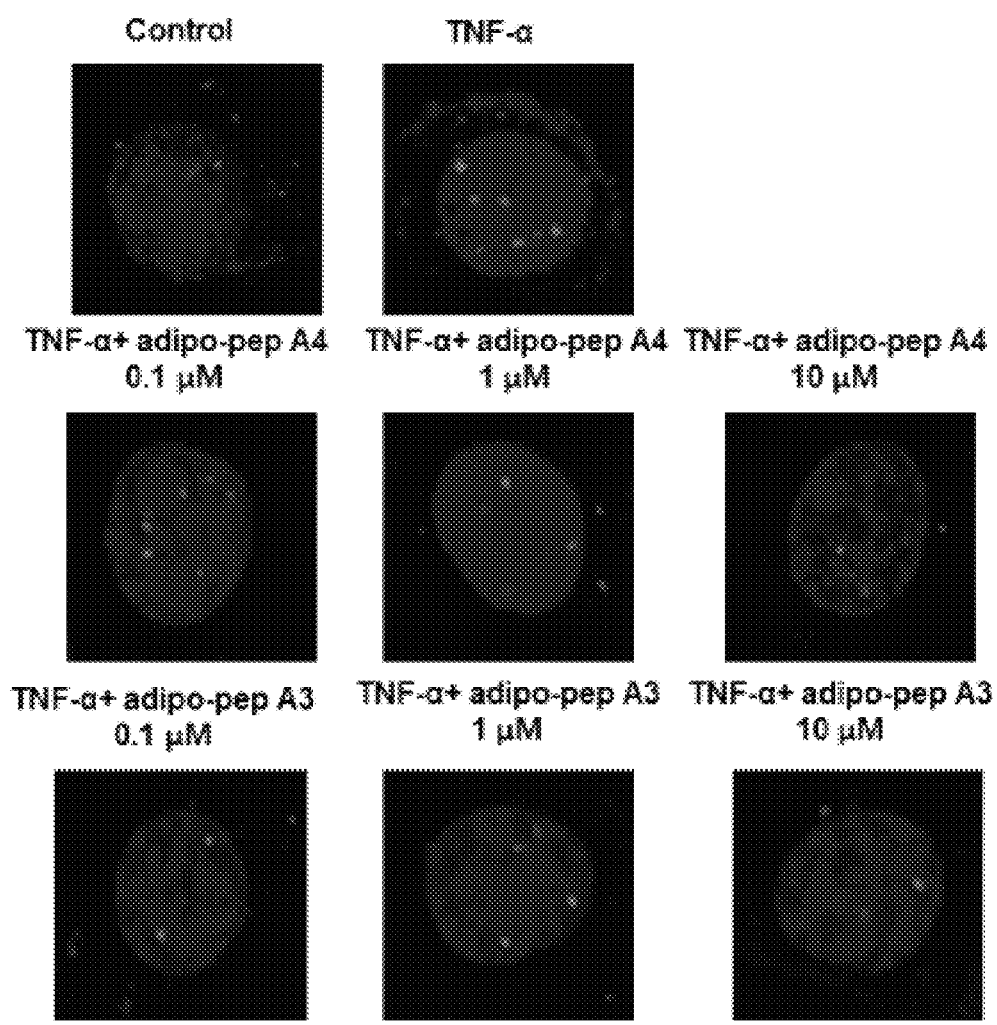

COMPOSITION COMPRISING PEPTIDE DERIVED FROM ADIPONECTIN

The Sequence Listing submitted in text format (.txt) filed on Mar. 15, 2016, named "SequenceListing.txt", created on Feb. 22, 2016, 1.17 KB), is incorporated herein by reference.

TECHNICAL FIELD

The present invention relates to a pharmaceutical or cosmetic composition comprising adiponectin-derived peptide fragments or small peptides. The peptides facilitate skin regeneration and moisturization, inhibit skin wrinkle, and have inhibitory activities against allergy and inflammation as well as metastasis of cancer cells.

BACKGROUND ART

Wounds, also referred to as skin lesions, show various symptoms, e.g., pain, bleeding, scar formation, dysfunction and so on. Wound healing involves processes such as inflammatory response, granulation tissue formation, re-epithelialization and angiogenesis etc. The processes include the actions of various growth factors, cytokines, neuronal hormones, etc. secreted from fibroblasts, adipocytes, blood-derived cells, and sensory neurons, leading to epidermal cell proliferation and extracellular matrix formation.

For regenerating connective tissues or maintaining the elasticity and strength of intact connective tissues without destruction thereof, it is important to form and maintain the extracellular matrix (ECM) proteins, such as type I, III collagens, elastin, fibronectin, etc., present in the skin. Natural aging or chronic exposure to ultraviolet radiation results in loss of the ECM proteins and reduced elasticity and strength of skin tissues, which are associated strongly with the characteristics of skin aging, such as wrinkle formation. Matrix metalloproteinases (MMPs) act as a key enzyme in degrading the dermal ECM. Over-expression of MMPs in keratinocytes and dermal fibroblasts under stress conditions, such as ultraviolet irradiation, contributes to degradation of the ECM proteins, thereby forming wrinkles on the skin.

An inflammatory response is known as a protective response of living organism for rehabilitating the structures and functions of tissues damaged by infection, trauma, etc. Mobilization of leukocytes to a focus of inflammation is critical for the rapid resolution of infections and restoration of tissue damages resulting from a variety of injuries. However, a misdirected or prolonged inflammatory response causes damage to the body's tissues or diseases. For example, inflammatory diseases are caused by bacterial or viral infection, e.g., cerebrospinal meningitis, enteritis, dermatitis, uveitis, encephalitis, or adult respiratory distress syndrome, or non-infectious factors, e.g., trauma, autoimmune diseases, or organ transplantation rejection. Inflammatory diseases are classified into acute and chronic inflammatory diseases according to symptoms or pathological features. Acute inflammation such as allergy or bacterial/viral infection is manifested as local signs such as a change in bloodstream, blood vessel size, and vascular permeability, and the recruitment of leukocytes. In contrast, a main pathological feature of chronic inflammation such as rheumatoid arthritis, artherosclerosis, chronic kidney infection, or hepatocirrhosis is a continuous emigration of macrophages, lymphocytes, or plasma cells into foci of inflammation due to recurrence of inflammatory factors, thereby causing a long-lasting inflammatory response.

In order to induce an inflammatory response, the emigration of leukocytes into inflammation foci is an essential event. Many cell adhesion molecules are implicated in the emigration of leukocytes. That is, the emigration of leukocytes includes a rolling stage in which leukocytes are mobilized to the blood vessels of inflamed sites by chemokine secreted from the inflamed sites and then rolled on surfaces of vascular endothelial cells while reducing the velocity of cell movement; an adhesion stage in which the leukocytes stops rolling and are firmly adhered to the vascular endothelial cells; and a transmigration stage wherein the leukocytes migrate through capillary vessels and basement membranes. The final stage, i.e., the transmigration stage is also called "diapedesis".

Cancer cells induced by carcinogens proliferate rapidly relative to normal cells, thereby forming tumor masses, invading surrounding tissues, and interfering with normal body functions. Cancer cells bring nutrients and oxygen by inducing angiogenesis, and metastasis thereof is also caused by angiogenesis. Although cancer cells grow infinitely at specific sites, they can also leave the sites from which they originated, migrate to and grow in new sites, whose process is called "metastasis". Metastasis involve several key steps: conversion of cancer cells to migratory mesenchymal cells, dissociation of the mesenchymal cells from the original tumor sites, invasion into and spread through surrounding connective tissues and capillary vessels, migration through blood vessels, escape from the blood vessels, migration through connective tissues, and proliferation in secondary sites.

Meanwhile, adiponectin is one of the adipokines, protein hormones secreted specifically in adipocytes. Adiponectin promotes the function of insulin and induces insulin resistance, thereby playing an important role in controlling cardiovascular diseases, such as hyperglycemia, hyperinsulinemia, obesity, and arteriosclerosis. And also, adiponectin has the functions for suppressing metastasis of cancer cells and inflammatory response. Adiponectin also performs the functions of wound healing, fibrosis inhibition, amelioration of skin wrinkle, and moisturization, by facilitating the expressions of filaggrin, hyaluronic acid, and extracellular matrix as well as the proliferation of keratinocytes in the skin.

DISCLOSURE

Technical Problem

The present inventors have found that the specific peptide fragments or small peptides derived from adiponectin facilitate the proliferation of fibroblasts and induce the formation of extracellular matrix such as collagen, thereby exhibiting excellent activities for wound healing and skin regeneration. And also, the present inventors have found that the specific peptide fragments induce the formation of skin barrier by facilitating the expression of filaggrin, thereby exhibiting skin moisturizing activity. In addition, the present inventors have found that the specific peptide fragments inhibit allergic reactions and inflammatory responses (especially, inflammatory responses in the skin) through inhibiting the transmigration of leukocytes; and inhibit the metastasis of cancer cells through inhibiting the invasion of cancer cells.

Therefore, it is an object of the present invention to provide a pharmaceutical and cosmetic composition comprising the specific peptide fragments derived from adiponectin as an active ingredient.

Technical Solution

In accordance with an aspect of the present invention, there is provided a pharmaceutical composition for preventing or treating a skin disease, comprising a peptide selected from the group consisting of the peptides of SEQ ID NOs: 1 to 6 as an active ingredient and a pharmaceutically acceptable carrier.

In the pharmaceutical composition of the present invention, the skin disease may be dermatitis, skin wrinkle, wound, or dry skin; preferably one or more dermatitis selected from the group consisting of allergic dermatitis, atopic dermatitis, contact dermatitis, acne vulgaris, ultraviolet radiation-induced dermatitis, eczema, and psoriasis.

In accordance with another aspect of the present invention, there is provided a cosmetic composition for inhibiting or improving a skin disorder, comprising a peptide selected from the group consisting of the peptides of SEQ ID NOs: 1 to 6 as an active ingredient.

In the cosmetic composition of the present invention, the skin disorder may be dermatitis, skin wrinkle, or dry skin, preferably skin wrinkle or dry skin.

Advantageous Effects

The peptides of the present invention, i.e., the peptides selected from the group consisting of the peptides of SEQ ID NOs: 1 to 6, facilitate the proliferation of fibroblasts and induce the formation of extracellular matrix such as collagen, thereby exhibiting excellent activities for wound healing and skin regeneration. And also, the peptides of the present invention induce the formation of skin barrier by facilitating the expression of filaggrin, thereby exhibiting skin moisturizing activity. Therefore, said peptides can be usefully applied to a pharmaceutical composition for wound healing or facilitating wound healing and a cosmetic composition for inhibiting wrinkle formation on the skin and for skin moisturization.

And also, the peptides of the present invention inhibit allergic reactions and inflammatory responses (especially, inflammatory responses in the skin) through inhibiting the transmigration of leukocytes; and inhibit the metastasis of cancer cells through inhibiting the invasion of cancer cells. Therefore, said peptides can be also usefully applied to a pharmaceutical composition for preventing or treating allergy or inflammatory diseases, a cosmetic composition for inhibiting or improving skin allergy or dermatitis, and a pharmaceutical composition for inhibiting metastasis of cancer cells.

BRIEF DESCRIPTION OF THE DRAWINGS

FIGS. 4a to 4d show the results obtained by evaluating the effects of the peptides of the present invention on the NF-κB activity.

BEST MODE

Figure 1:
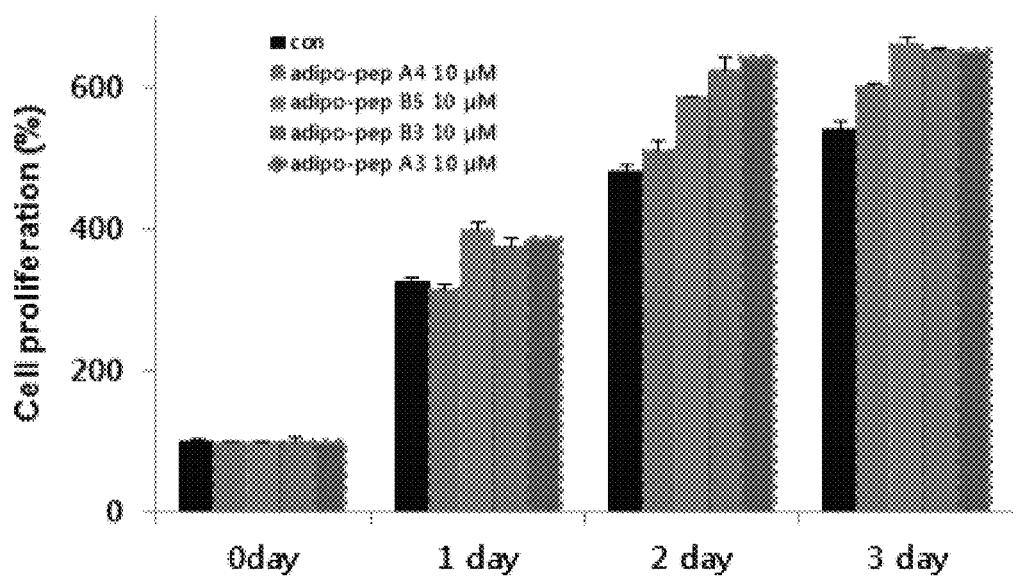
FIG. 1 shows the results obtained by evaluating the effects of the peptides of the present invention on the proliferation of fibroblasts.

Throughout the specification, the term "skin disease" includes all the skin diseases, especially the diseases caused by abnormalities in the adiponectin-mediated skin functions. Examples of the skin disease include dermatitis, skin wrinkle, wound, and dry skin. Said dermatitis includes allergic dermatitis, atopic dermatitis, contact dermatitis, acne vulgaris (or acneiform eruption), ultraviolet radiation-induced dermatitis, eczema, psoriasis, and so on. Said skin wrinkle includes the wrinkles according to UV stimulation and/or aging. Said wound includes a burn or a skin damage caused by UV stimulation. Said dry skin includes xeroderma, Sjogren's syndrome, and so on.

The term "skin disorder" includes all the skin disorders, especially the disorders caused by abnormalities in the adiponectin-mediated skin functions. Examples of the skin disorder include dermatitis, skin wrinkle, and dry skin. Said dermatitis includes allergic dermatitis, atopic dermatitis, contact dermatitis, acne vulgaris, ultraviolet radiation-induced dermatitis, eczema, psoriasis, and so on. Said skin wrinkle includes the wrinkles according to UV stimulation and/or aging. Said dry skin includes xeroderma, Sjogren's syndrome, and so on.

The present inventors prepared various fragments derived from adiponectin and investigated the activities thereof. Surprisingly, the present inventors have found that the specific small peptide fragments having 3 to 5 amino acids derived from adiponectin facilitate the proliferation of fibroblasts and induce the formation of extracellular matrix such as collagen, thereby exhibiting excellent activities for wound healing and skin regeneration. And also, the present inventors have found that said peptide fragments induce the formation of skin barrier by facilitating the expression of filaggrin, thereby exhibiting skin moisturizing activity. In addition, the present inventors have found that said peptide fragments inhibit allergic reactions and inflammatory responses (especially, inflammatory responses in the skin) through inhibiting the transmigration of leukocytes; and inhibit the metastasis of cancer cells (especially, skin cancer cells) through inhibiting the invasion of cancer cells. The peptide fragments are shown in the following Table 1.

TABLE 1

| Peptide name | SEQ ID NO | Amino acid sequence |
| --- | --- | --- |
| adipo-pep A4 | SEQ ID NO: 1 | Tyr-His-Ile-Thr |
| adipo-pep A3 | SEQ ID NO: 2 | His-Ile-Thr |
| adipo-pep B5 | SEQ ID NO: 3 | Leu-Phe-Thr-Tyr-Asp |
| adipo-pep B4 | SEQ ID NO: 4 | Leu-Phe-Thr-Tyr |
| adipo-pep B3 | SEQ ID NO: 5 | Phe-Thr-Tyr |
| adipo-pep C3 | SEQ ID NO: 6 | His-Leu-Thr |

Therefore, the present invention provides a pharmaceutical composition for preventing or treating a skin disease, comprising a peptide selected from the group consisting of the peptides of SEQ ID NOs: 1 to 6 as an active ingredient and a pharmaceutically acceptable carrier. In the pharmaceutical composition of the present invention, the skin disease may be dermatitis, skin wrinkle, wound, or dry skin; preferably one or more dermatitis selected from the group consisting of allergic dermatitis, atopic dermatitis, contact dermatitis, acne vulgaris, ultraviolet radiation-induced dermatitis, eczema, and psoriasis.

The present invention also provides a pharmaceutical composition for inhibiting cancer metastasis, preferably for inhibiting skin cancer metastasis, comprising a peptide selected from the group consisting of the peptides of SEQ ID NOs: 1 to 6 as an active ingredient and a pharmaceutically acceptable carrier.

The pharmaceutical composition of the present invention may include a pharmaceutically acceptable carrier, for example additives such as lactose or corn starch, lubricants such as magnesium stearate, currently available emulsifiers, suspending agents, buffers, isotonic agents, etc. The pharmaceutical composition of the present invention can be administered in an oral or a parenteral dosage form, preferably in a parenteral dosage form. For intramuscular, intraperitoneal, subcutaneous, or intravenous administration, a sterilized solution of an active ingredient is generally prepared. In this case, the sterilized solution may include a buffer to achieve a desired pH value. With respect to formulations for intravenous administration, an isotonic agent may be used to render the formulations isotonic. The pharmaceutical compositions of the present invention can be formulated into aqueous solutions including a pharmaceutically acceptable carrier such as a saline of pH 7.4. The aqueous solutions can be introduced into a patient's intramuscular blood stream by local bolus injection. The pharmaceutical composition of the present invention can be administered to patients who suffer from various skin diseases and cancers such as skin allergy, dermatitis, skin wrinkle, wound, dry skin, etc. at a daily dosage of about 1 to 2000 mg/kg. An adequate dosage is generally changed according to age, body weight, and conditions of a patient.

And also, the present invention includes within its scope a functional cosmetic composition comprising said peptides as an active ingredient. That is, the present invention provides a cosmetic composition for inhibiting or improving a skin disorder, comprising a peptide selected from the group consisting of the peptides of SEQ ID NOs: 1 to 6 as an active ingredient. In the cosmetic composition of the present invention, the skin disorder may be dermatitis, skin wrinkle, or dry skin, preferably skin wrinkle or dry skin.

The cosmetic composition of the present invention may be prepared in various forms according to conventional methods thereof. For example, the cosmetic composition may be prepared in forms of cosmetic products, cosmetic solutions, creams, lotions, etc., which may be diluted with a cleansing water, an astringent solution, or a moisture solution, for the use thereof. And also, the cosmetic composition may include conventional excipients, such as a stabilizer, a solubilizing agent, vitamin, a pigment, a flavoring agent, which are conventionally used in the field of cosmetic composition. In the cosmetic composition, said peptides may be present in an amount enough to provide the effects for improving skin allergy or inflammation, for example in an amount ranging from 0.001 to 10 weight %, preferably about 0.01 to 1 weight %, based on the total weight of the composition.

Hereinafter, the present invention will be described more specifically by the following examples and experimental examples. However, the following examples and experimental examples are provided only for illustrations and thus the present invention is not limited to or by them.

EXAMPLE 1

Synthesis of Peptides

The peptides of SEQ ID NOs: 1 to 6 (in the above Table 1) were synthesized with an automatic peptide synthesizer (PeptrEx-R48, Peptron, Daejeon, Korea) using a FMOC solid-phase method. The synthesized peptides were purified and analyzed by reverse-phase high-performance liquid chromatography (reverse-phase HPLC) (Prominence LC-20AB, Shimadzu, Japan) using a C18 analytical RP column (Shiseido capcell pak), and isolated using a mass spectrometer (HP 1100 Series LC/MSD, Hewlett-Packard, Roseville, U.S.A.).

EXAMPLE 2

Preparation of Peptide-containing Compositions

The peptides of SEQ ID NOs: 1 to 6 were respectively dissolved in phosphate buffered saline (PBS) to a concentration of 1 M. The resultant protein solutions were diluted with PBS and then used in the following experimental examples.

EXPERIMENTAL EXAMPLE 1

Tests For Facilitating The Proliferation Of Mouse Fibroblast Cell Line NIH3T3

The NIH3T3 cells (mouse fibroblast cell line, ATCC CRL-1658, USA), along with 100 μl of Dulbecco's Modified Eagle medium (DMEM), were added to each well of the 96-well microplate in the concentration of $5 \times 10^3$ cells per well, and then cultured in a 5% $CO_2$ incubator at 37° C. for 24 hours. The peptide solutions (100 μl) having the respective peptide of SEQ ID NOs: 1, 2, 3 and 5 in the concentration of 10 μM were added to each well. While incubating the cells for 24, 48, and 72 hours therefrom, 10 μl of CCK-8 (Dojindo Laboratories, Japan) was added to each well and then the respective absorbance at 475 nm was measured with Spectramax plus 190 plate reader (Molecular Devices, USA). The results thereof are shown in FIG. 1. As shown in FIG. 1, the proliferations of NIH3T3 cells were significantly increased in the groups treated with the peptides of SEQ ID NOs: 1, 2, 3 and 5. These results show that the peptides of the present invention have wound-healing and skin-regenerating activities through facilitating the proliferation of fibroblasts.

EXPERIMENTAL EXAMPLE 2

Evaluation on Activation of the Procollagen Type-1 Expression in Fibroblasts

Figure 2:
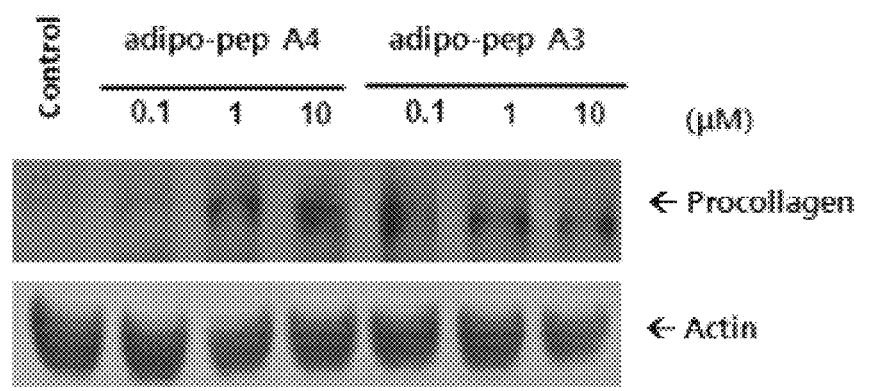
FIG. 2 shows the results obtained by evaluating the effects of the peptides of the present invention on the collagen synthesis in fibroblasts.
Figure 2:
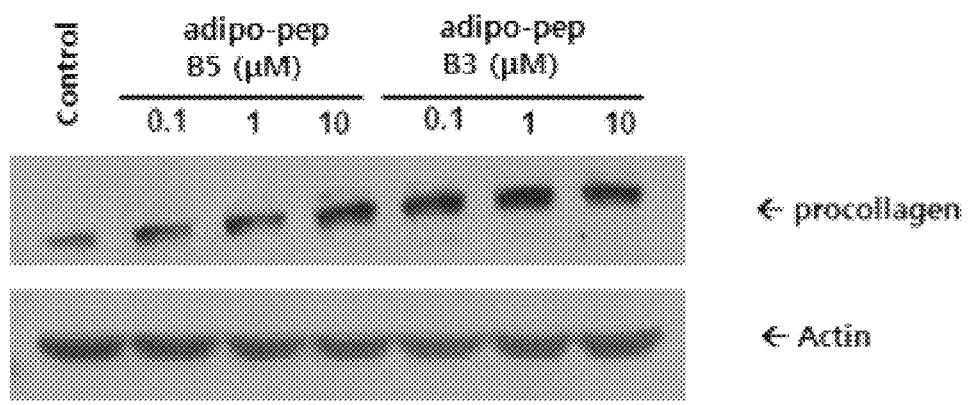

Since facilitation of the collagen fiber synthesis is one of the principal means for inhibiting skin aging, we evaluate whether the collagen synthesis in fibroblasts is facilitated by the treatment of the peptides of the present invention, using the NIH3T3 cells (mouse fibroblast cell line, ATCC CRL-1658, USA). The fibroblasts were treated with the peptides of SEQ ID NOs: 1, 2, 3 and 5, in the concentrations of 0.1, 1 and 10 μM, respectively. After 48 hours, the cell extracts were subject to the Western blotting assay so as to measure the expressions of procollagen type-1. The results thereof are shown in FIG. 2. As shown in FIG. 2, the expressions of procollagen type-1 were increased by the treatment of the peptides of SEQ ID NOs: 1, 2, 3 and 5 in concentration-dependent manner. Therefore, it can be seen that the peptides of the present invention can inhibit skin aging derived from loss of collagen, especially skin wrinkle.

EXPERIMENTAL EXAMPLE 3

Figure 3:
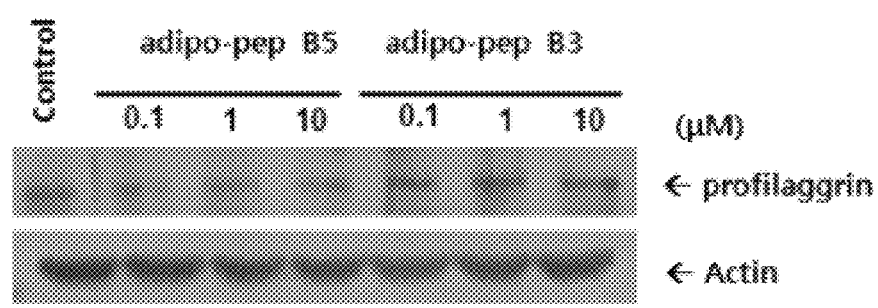
FIG. 3 shows the results obtained by evaluating the effects of the peptides of the present invention on the profilaggrin synthesis.
Figure 4B:
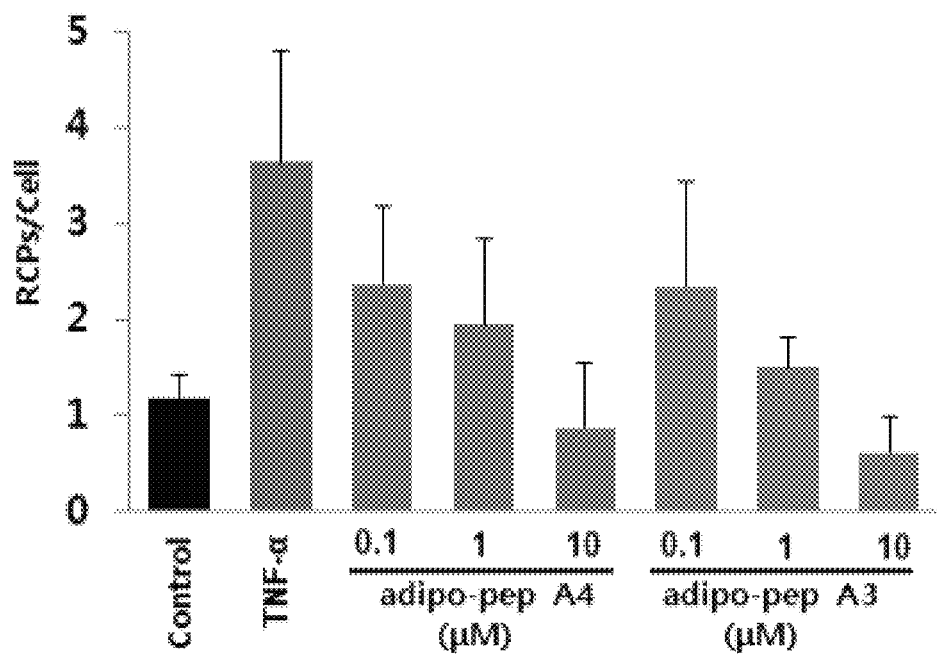
Figure 4C:
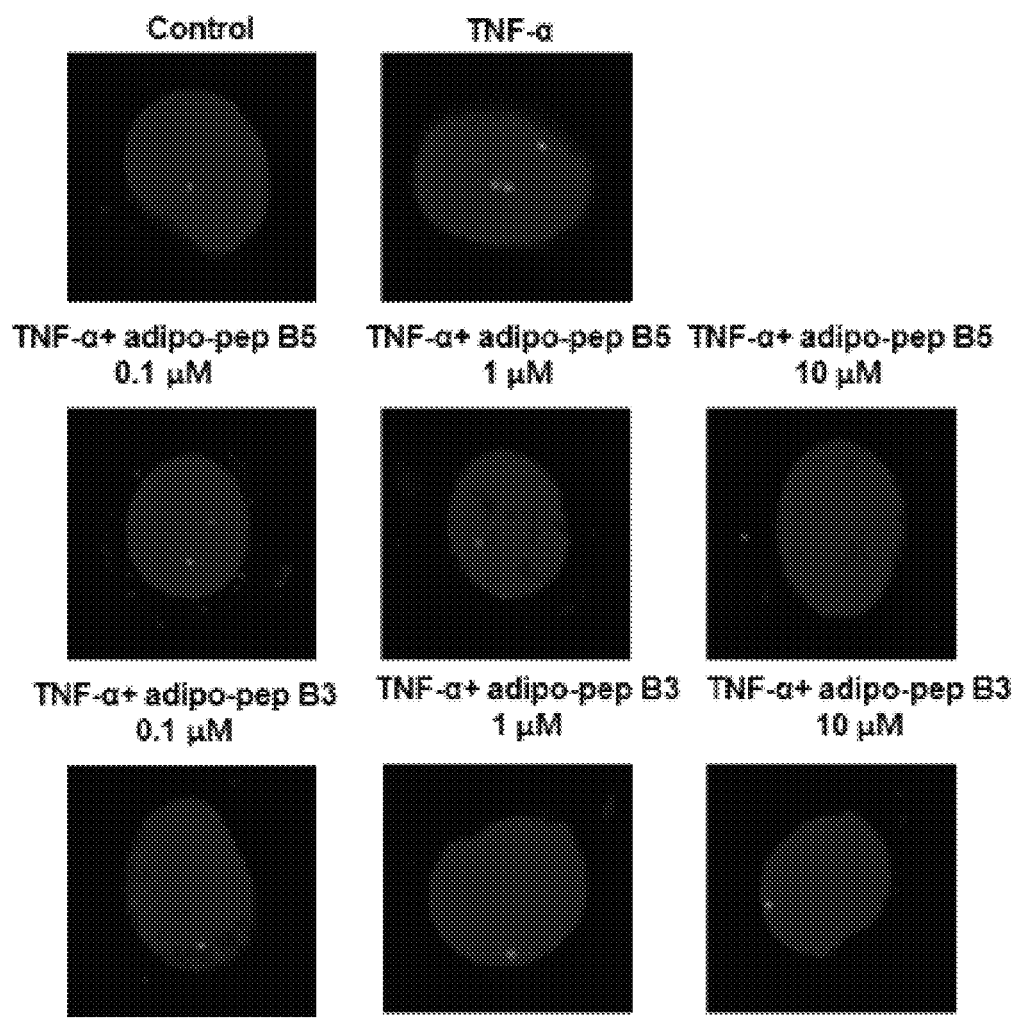
Figure 4D:
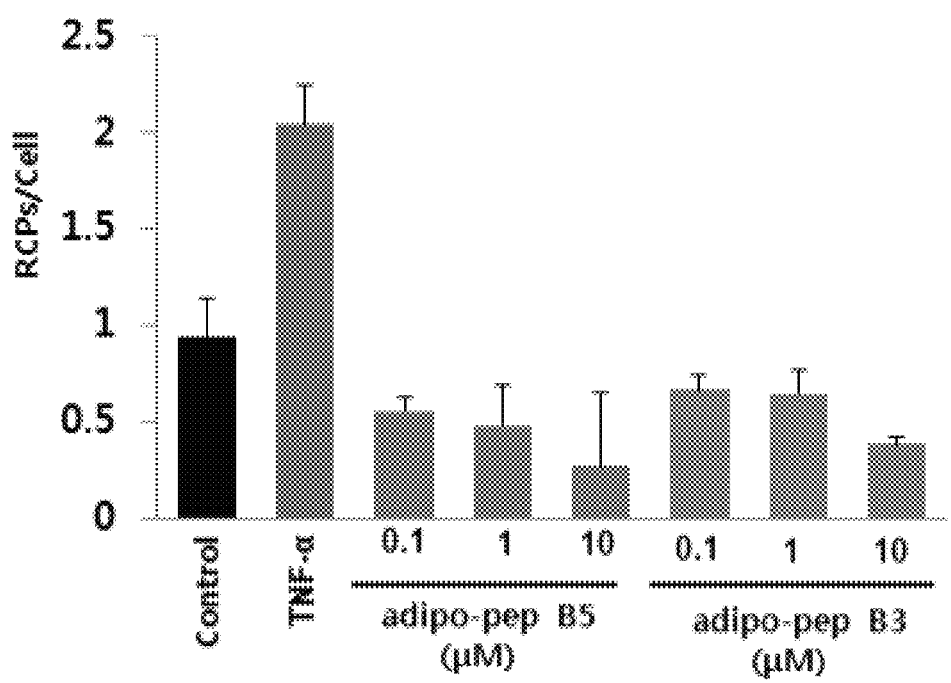

Evaluation on Control of the Profilaggrin Expression in Human Keratinocyte Cell Line HaCaT Since profilaggrin is one of the principal elements for constituting skin barrier, we evaluate whether the profilaggrin synthesis in keratinocytes is facilitated by the treatment of the peptides of the present invention, using the HaCaT cells (human keratinocyte cell line, DKFZ, Heidelberg, Germany). The HaCaT cells were treated with the peptides of SEQ ID NOs: 3 and 5, in the concentrations of 0.1, 1.0 and 10 µM. After 48 hours, the cell extracts were subject to the Western blotting assay so as to measure the expressions of profilaggrin. The results thereof are shown in FIG. 3. As shown in FIG. 3, the expressions of profilaggrin were increased by the treatment of the peptides of SEQ ID NOs: 3 and 5 in concentration-dependent manner. Therefore, it can be seen that the peptides of the present invention have a skin-moisturizing activity through facilitating the profilaggrin expression.

EXPERIMENTAL EXAMPLE 4

Tests for Inhibition of NF-κB Activity

Effects of the peptides of the present invention on activation of the transcription factor NF-κB was analyzed according to the in situ proximity ligation assay method. The analysis was performed using the Duolink® In Situ reagent (Olink Bioscience, Sweden).

The NIH3T3 cells ($2.5 \times 10^4$ cells) were plated in the 24-well plate, each well having a 12-mm glass in the bottom. The cells were stabilized for 24 hours and then treated with the peptides of SEQ ID NOs: 1, 2, 3 and 5, in the concentrations of 0.1, 1.0 and 10 µM. After 1 hour from the treatments, the cells of each well were treated with TNF-α (25 µg/ml) for 2 hours. After the cells fixed with 4% paraformaldehyde were treated with 0.1% Triton-X, a drop of the blocking solution was added to the cells, which were then incubated at 37° C. for 30 minutes. For measuring levels of the translocation of NF-κB into the nucleus, the cells were treated with the anti-p50 mouse monoclonal antibody (NFκB p50 (4D1): sc-53744, Santa Cruz Biotechnology, INC., USA) and the anti-p65 rabbit monoclonal antibody (NF-κB p65 (D14E12) XP® rabbit mAb, Cell signaling Technology, USA) at 37° C. After 30 minutes therefrom, the cells were treated with the PLA probe solution at 37° C. for 1 hour, with the ligation solution for 30 minutes, and then with the amplification solution for 100 minutes. After washing the cells, the number of the spots translocated into the nucleus among the NF-κB shown in red spots was measured with a confocal microscopy. The results thereof are shown in FIGS. 4a to 4d. As shown in FIGS. 4a to 4d, the translocations in the groups treated with the peptides of SEQ ID NOs: 1 2, 3 and 5 were significantly reduced (about 25~60% reduction) as compared with that in the control group. These results show that the peptides of the present invention inhibit activation of the NF-κB which plays a critical role in the synthesis of inflammatory cytokines.

EXPERIMENTAL EXAMPLE 5

Figure 5:
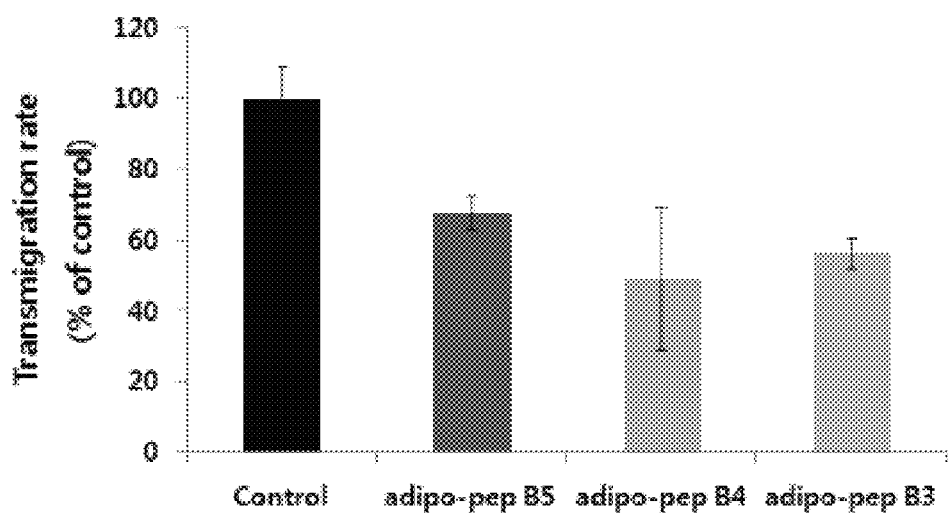
FIG. 5 shows the results obtained by measuring the transmigration of the human monocyte cell line (U937), after the treatment with the peptides of the present invention.

Tests for Inhibitory Activity Against in vitro Trans-endothelial Migration of Monocytes Human umbilical vein endothelial cells (HUVECs) were cultured in the upper compartments of Boyden chambers. The supernatants were removed, and human monocytes (U937), which had been untreated or treated with the protein solutions including the peptide of SEQ ID NOs: 3 to 5 (30 µg/ml) prepared in Example 2 for 1 hour, were seeded at $2 \times 10^5$ cells/chamber. At this time, a culture including a supernatant obtained by centrifugation of the culture obtained after culturing NIH/3T3 mouse fibroblasts in serum-free DMEM containing 0.005% vitamin C and 0.1% Bovine Serum Albumin (BSA) for 16 hours was placed in the lower compartments of the chambers to induce the invasion of the monocytes. The chambers were incubated for 6 hours, and the number of the cells migrated to the lower compartments was measured. The test was repeated three times, and the results are shown in FIG. 5. The control group was treated with only PBS having no peptide. As shown in FIG. 5, the numbers of migrated monocytes in the groups treated with the peptides of the present invention were significantly reduced (about 50-70% reduction) as compared with that in the control group. Taking into consideration that transmigration is essential for migration of leukocytes into inflammation sites through blood vessels, it is expected that peptides of the present invention can effectively inhibit the inflammatory reaction.

EXPERIMENTAL EXAMPLE 6

Tests for Inhibitory Activity Against Invasion of Cancer Cells

Figure 6:
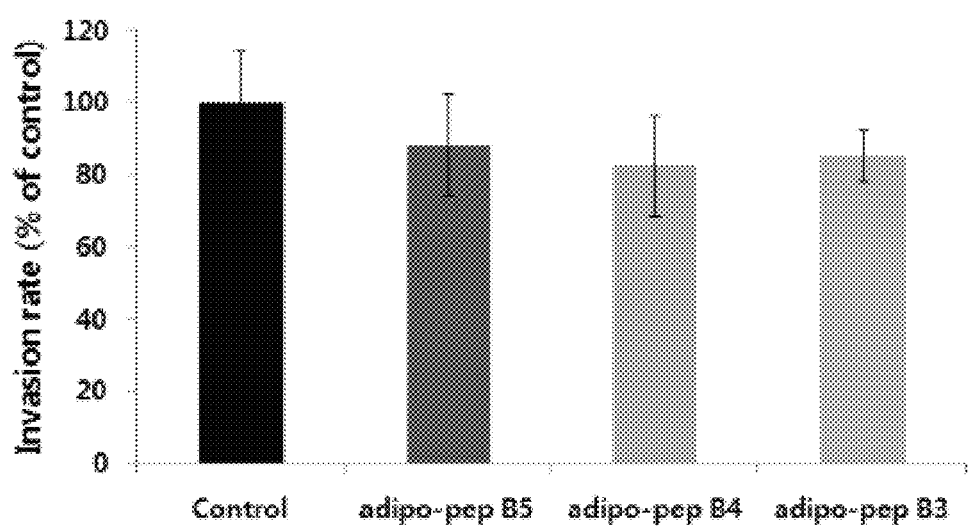
FIG. 6 shows the results obtained by measuring the invasion of the human breast cancer cell line (MCF-7) into matrigel, after the treatment with the peptides of the present invention.

After matrigel, basement membrane components, is subject to polymerization reaction in a transwell, human breast cancer cells MCF-7 cells ($1.5 \times 10^5$ cells) were loaded to the upper compartment of the transwell and then treated with each peptide of SEQ ID NOs: 3 to 5 in the concentration of 1 µM. The cells were cultured in a 5% $CO_2$ incubator at 37° C. 0.1% BSA was added to the upper compartment of the transwell. After an invasion-inducing medium (the supernatant isolated after culturing NIH 3T3 cells in the serum-free DMEM containing 0.005% vitamin C and 0.1% bovine serum albumin for 24 hours) was placed in each lower compartment, cells migrated into the lower compartments of the transwell were counted three times at 24-hour intervals, and then the results were statistically analyzed. The control group was treated with only PBS having no peptide. The results thereof are shown in FIG. 6. As shown in FIG. 6, the base membrane invasion rates of the human breast cancer cells in the groups treated with the peptides of SEQ ID NOs: 3 to 5 of the present invention were reduced by about 80% as compared with that in the control group. Taking into consideration that cancer cells come out from blood vessels and invade basement membranes or surrounding connective tissues and then spread to secondary sites, it can be seen that the peptides of the present invention can effectively inhibit the metastasis of cancer cells.

The invention claimed is:

1. A peptide for facilitating expression of filaggrin, inducing formation of skin barrier, or inhibiting metastasis of cancer cells, selected from the group consisting of the peptides of SEQ ID NOs: 1 to 4 and 6.

2. A pharmaceutical composition, comprising a peptide selected from the group consisting of the peptides of SEQ ID NOs: 1 to 4 and 6 and a pharmaceutically acceptable carrier selected from the group consisting of saline, lactose, corn starch, a lubricant, an emulsifier, a suspending agent, a buffer, and an isotonic agent.

3. A method for improving or treating dermatitis, skin wrinkle, wound, or dry skin, comprising administering to a subject in need thereof an effective amount of a peptide selected from the group consisting of the peptides of SEQ ID NOs: 1 to 6.

4. The method of claim 3, wherein the dermatitis is one or more selected from the group consisting of allergic dermatitis, atopic dermatitis, contact dermatitis, acne vulgaris, ultraviolet radiation-induced dermatitis, eczema, and psoriasis.

* * * * *

SEQUENCE LISTING

```
<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<223> OTHER INFORMATION: Peptide fragment

<400> SEQUENCE: 1

Tyr His Ile Thr
  1

<210> SEQ ID NO 2
<211> LENGTH: 3
<212> TYPE: PRT
<213> ORGANISM: Artificial Sequence
<220> FEATURE:
<223> OTHER INFORMATION: Peptide fragment

<400> SEQUENCE: 2

His Ile Thr
  1

<210> SEQ ID NO 3
<211> LENGTH: 5
<212> TYPE: PRT
<213> ORGANISM: Artificial Sequence
<220> FEATURE:
<223> OTHER INFORMATION: Peptide fragment

<400> SEQUENCE: 3

Leu Phe Thr Tyr Asp
  1               5

<210> SEQ ID NO 4
<211> LENGTH: 4
<212> TYPE: PRT
<213> ORGANISM: Artificial Sequence
<220> FEATURE:
<223> OTHER INFORMATION: Peptide fragment

<400> SEQUENCE: 4

Leu Phe Thr Tyr
  1

<210> SEQ ID NO 5
<211> LENGTH: 3
<212> TYPE: PRT
<213> ORGANISM: Artificial Sequence
<220> FEATURE:
<223> OTHER INFORMATION: Peptide fragment

<400> SEQUENCE: 5

Phe Thr Tyr
  1

<210> SEQ ID NO 6
<211> LENGTH: 3
<212> TYPE: PRT
<213> ORGANISM: Artificial Sequence
<220> FEATURE:
<223> OTHER INFORMATION: Peptide fragment
```

```
<400> SEQUENCE: 6

His Leu Thr
 1
```